United States Patent [19]
Shaw et al.

[11] Patent Number: 5,989,220
[45] Date of Patent: Nov. 23, 1999

[54] SELF-RETRACTING IV CATHETER INTRODUCER

[75] Inventors: Thomas J. Shaw, Little Elm; Kathryn Duesman, Pilot Point, both of Tex.

[73] Assignee: Retractable Technologies Inc., Little Elm, Tex.

[21] Appl. No.: 09/085,496

[22] Filed: May 26, 1998

[51] Int. Cl.⁶ .......................... A61M 5/162; A61M 5/00
[52] U.S. Cl. ........................................ 604/110; 604/165
[58] Field of Search .................................. 604/110, 165, 604/164

[56] References Cited

U.S. PATENT DOCUMENTS

| | | |
|---|---|---|
| 4,747,831 | 5/1988 | Kulli . |
| 4,828,548 | 5/1989 | Walter . |
| 4,906,236 | 3/1990 | Alberts et al. ........................ 604/164 |
| 4,935,014 | 6/1990 | Haber ................................. 604/110 |
| 4,994,034 | 2/1991 | Botich et al. . |
| 5,007,901 | 4/1991 | Shields ............................... 604/110 |
| 5,019,044 | 5/1991 | Tsao . |
| 5,024,665 | 6/1991 | Kaufman . |
| 5,114,410 | 5/1992 | Battle . |
| 5,129,884 | 7/1992 | Dysarz . |
| 5,207,647 | 5/1993 | Phelps . |
| 5,267,961 | 12/1993 | Shaw . |
| 5,376,080 | 12/1994 | Petrussa ............................. 604/110 |
| 5,385,551 | 1/1995 | Shaw . |
| 5,389,076 | 2/1995 | Shaw . |
| 5,407,431 | 4/1995 | Botich et al. . |
| 5,407,436 | 4/1995 | Toft et al. . |
| 5,423,758 | 6/1995 | Shaw . |
| 5,501,675 | 3/1996 | Erskine . |
| 5,531,701 | 7/1996 | Luther ............................... 604/165 |
| 5,562,629 | 10/1996 | Haughton et al. . |
| 5,573,510 | 11/1996 | Isaacson . |
| 5,575,777 | 11/1996 | Cover et al. . |
| 5,578,011 | 11/1996 | Shaw . |
| 5,613,952 | 3/1997 | Pressly, Sr. et al. . |
| 5,700,250 | 12/1997 | Erskine ............................. 604/165 |
| 5,752,936 | 5/1998 | Chien ............................... 604/110 |
| 5,797,880 | 8/1998 | Erskine ............................. 604/110 |
| 5,817,058 | 10/1998 | Shaw ................................ 604/110 |
| 5,899,883 | 5/1999 | Chern et al. ........................ 604/110 |

*Primary Examiner*—Paul J. Hirsch
*Attorney, Agent, or Firm*—Locke Liddell & Sapp LLP

[57] ABSTRACT

A self-retracting IV catheter introducer automatically retracts the catheter needle safely within a housing when the connector attached to the cannula is separated from the housing after the cannula has been inserted into a patient. In one embodiment the housing comprises a retraction tube enclosing a retraction body having a rear portion mounted within the retraction tube and a front portion carrying a needle and extending through an opening in the front of the retraction body. A connection surface on the exposed front of the retraction body is frictionally engaged with a corresponding connection surface on the connector. Abutting surfaces between the connector and the retraction tube serve as stops. Releasable frictional engagement of the connection surfaces prevents retraction. In a second embodiment the front portion of the retraction tube extends forwardly configured as springing arms having a protrusion which engages a depression in the outer surface of an extending front portion of the retraction body. The springing arms are forcibly pressed against the front portion of the retraction body when a connector for the cannula is forcibly slidably placed over the springing arms. When the connector is separated, the arms are free to spring open releasing the retraction body for complete retraction into the retraction tube along with the needle.

28 Claims, 4 Drawing Sheets

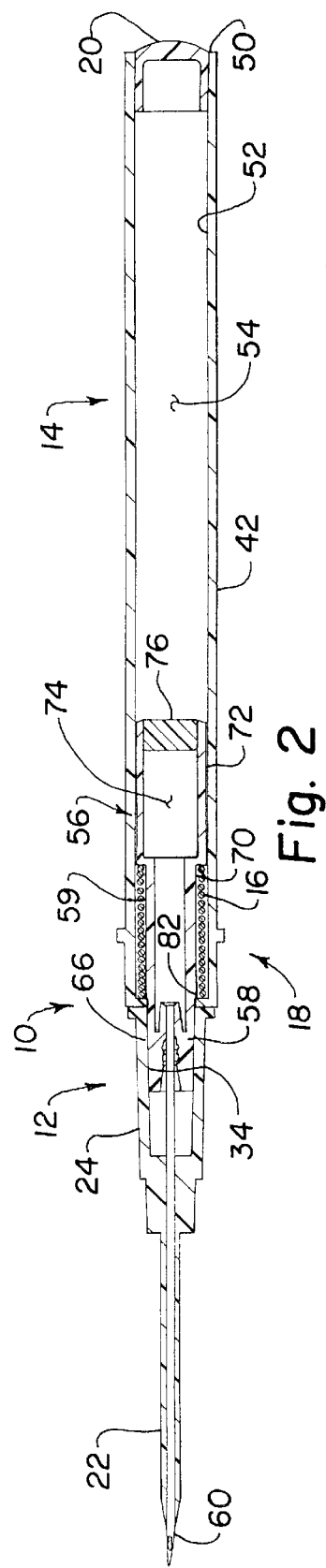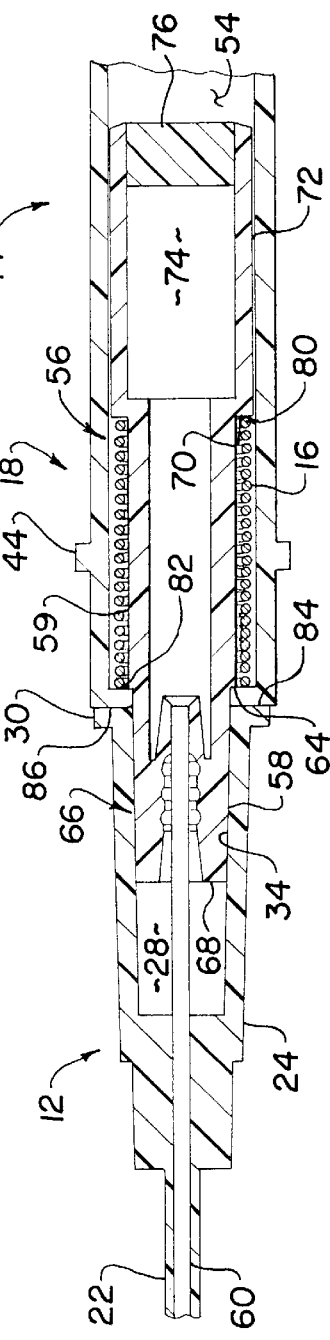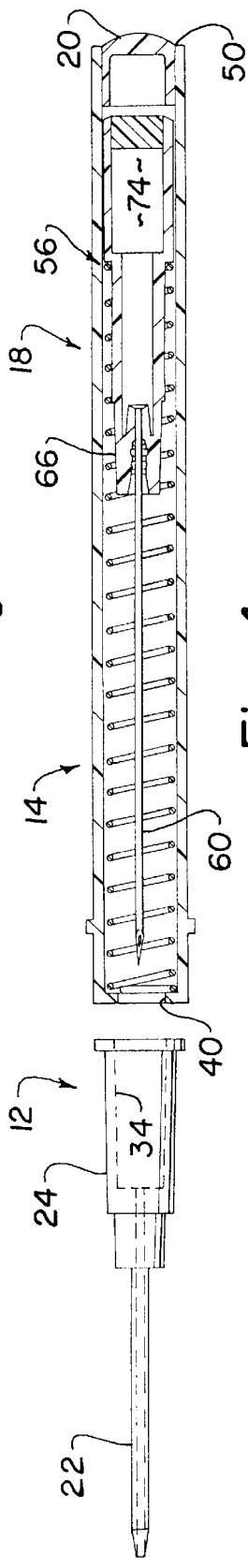

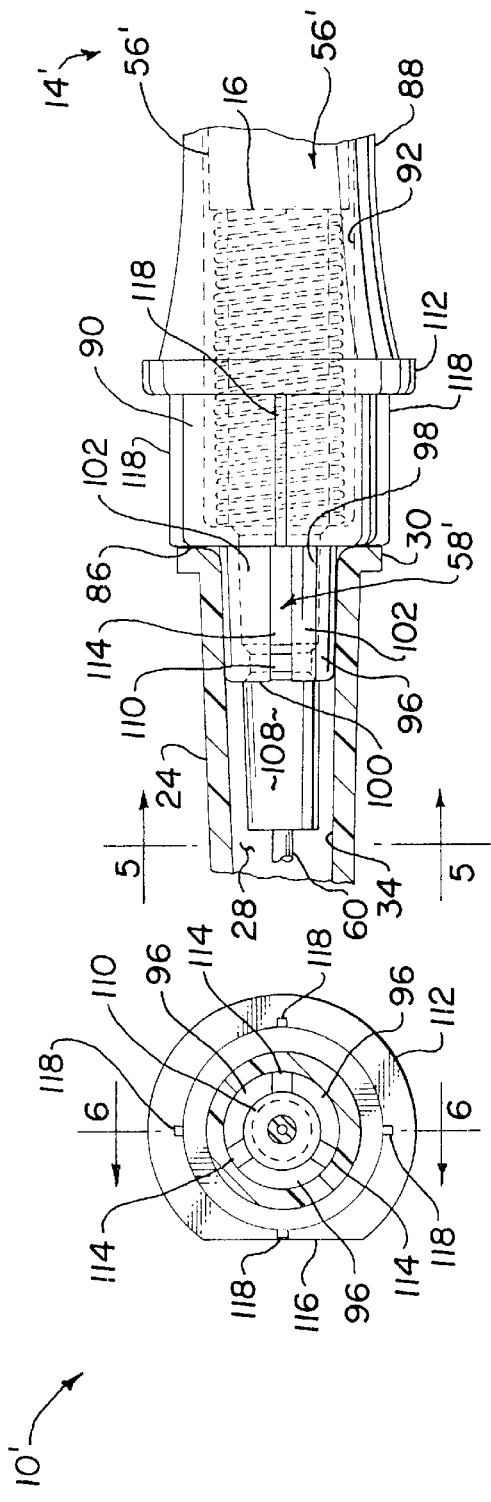
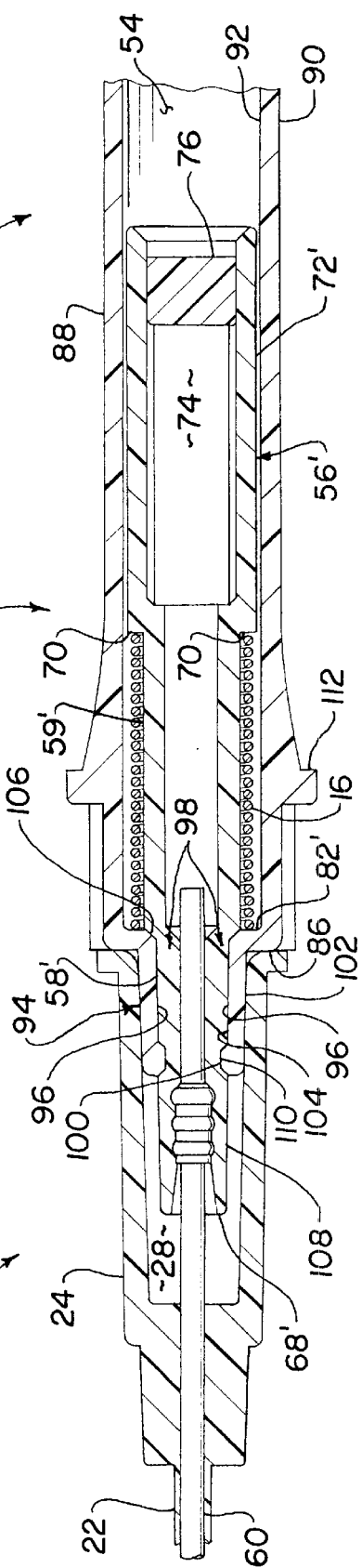
Fig. 5
Fig. 7
Fig. 6

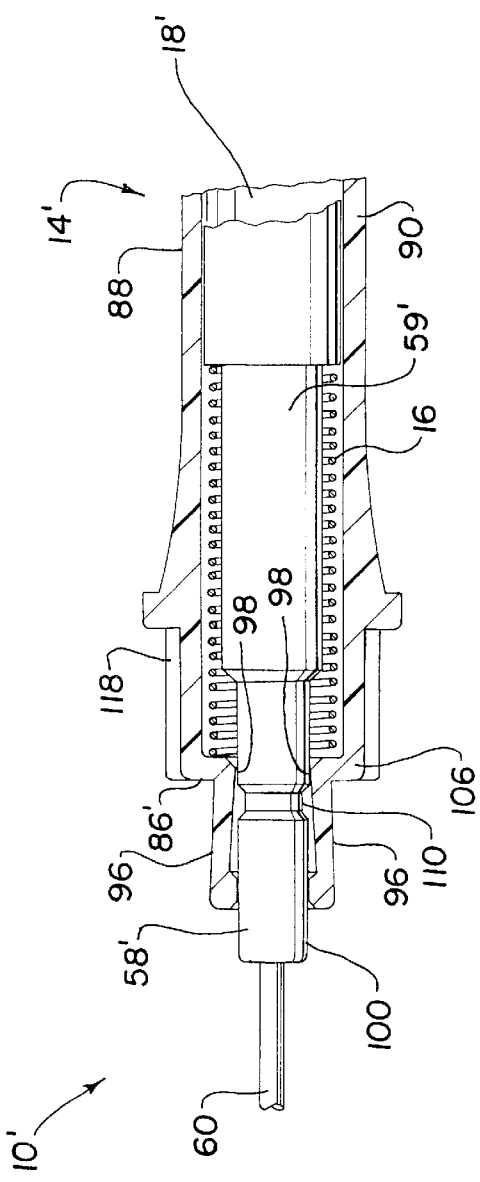
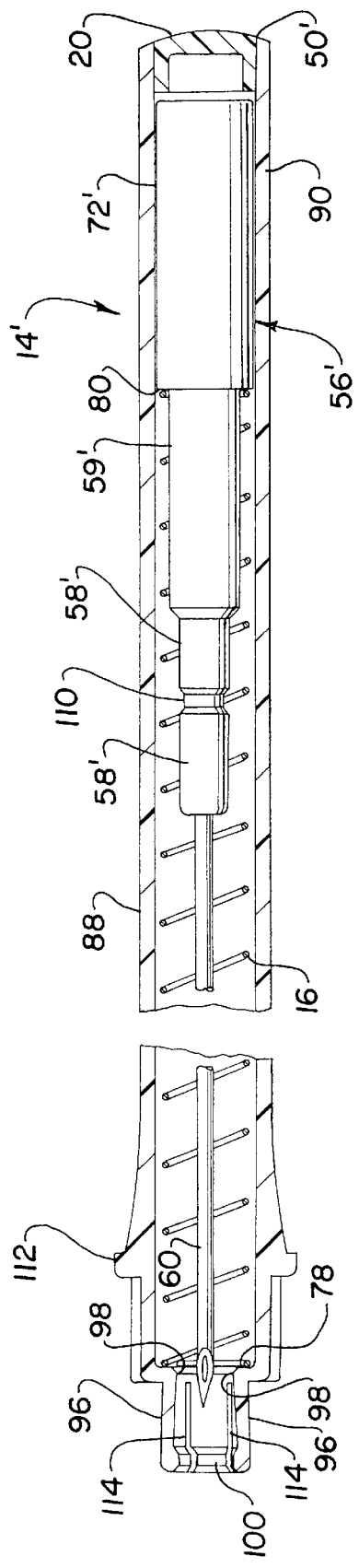
Fig. 8
Fig. 9

SELF-RETRACTING IV CATHETER INTRODUCER

BACKGROUND OF THE ART

1. Field of the Invention

The invention is a medical device designed to facilitate insertion of a catheter into a patient's body.

2. Background of the Prior Art

Catheter insertion devices are well known in the art. When a catheter is inserted into a patient for the intravenous delivery of a fluid, a disposable needle passing through the catheter cannula is utilized to make a puncture to permit entry of the tip of the cannula into the patient. The needle is then withdrawn leaving the catheter in place either for a direct hook up to a bottle of fluid to be delivered, or to be capped for later use. The needle which is now contaminated with blood or other body fluid must be disposed of without creating a risk of needle sticks to medical personnel which are engaged in the operation of inserting a catheter. A danger to clean up and medical waste disposal personnel continues if the used needles are not rendered harmless in some way. Caps or covers that can be mounted over the needle are not a satisfactory solution because they must be put in place and can come loose and expose the used needle. An excellent discussion of the problems associated with various approaches and uses of cannula insertion products is found in Kulli, U.S. Pat. No. 4,747,831 which is incorporated herein by reference.

Retractable needles have been recognized as the best solution of these problems. A number of these approaches are disclosed in U.S. Pat. No. 4,747,831, mentioned above, which includes an external latch mechanism which is pushed to release a spring loaded needle which is withdrawn into the chamber of the device. Some embodiments have a sliding block and retractable fingers which depress spring loaded ears to allow retraction of the needle holder, racheting devices which unlatch the needle holder by rotation of parts and even frangible parts which are broken when a plunger is pushed forward. Dysarz, U.S. Pat. No. 5,129,884 is another example of an external latch which may be disengaged to allow a needle holder to withdraw a needle into the main body of the device. Walter, U.S. Pat. No. 4,828,548 discloses a holder having a piston which may be operated on by vacuum to withdraw a needle. Erskine, U.S. Pat. No. 5,501,675 is a more recent version of a latch operated device wherein a needle holding part may be released with an external latch.

The devices of the prior art often have too many complicated parts which are difficult to manufacture and especially difficult to assembly in a high speed manufacturing operation. Many of them are prone to premature firing during handling and with some it is difficult to know when the needle is safe. Disengagement of the catheter assembly from the retraction device is not fully under the timing and control of the medical operator because retraction results in immediate separation of the device form the cannula assembly. With the present invention, the assembled catheter introducer is handled as a unit. When the operator verifies that the needle is properly inserted, one hand can hold the connector that remains attached to the patient while the other hand separates the retraction body which upon separation is automatically retracted without the necessity of locating or pushing any buttons or movable parts. A portion of the hand rests against the cannula to prevent blood flow until the other hand inserts the conventional tube into the catheter connector to start the infusion of fluid. Immediately after separation the retraction body safely contains the retracted needle and the removed part is safely discarded.

SUMMARY OF THE INVENTION

A self-retracting IV catheter introducer illustrated in two embodiments is especially well suited for automated mass production and assembly. In both embodiments a handle portion comprising a retraction tube has an exposed front portion frictionally and releasably engaged into the open back end of a conventionally shaped connector of a cannula used to introduce fluids into a patient's body. When the handle portion comprising a retraction tube and a retraction body is hand separated from the cannula connector, retraction of the retraction body carrying the hard needle automatically and immediately takes place.

In the first embodiment, a retraction tube having a front end portion with an open mouth and a back end portion comprises a handle containing a retraction body configured for lineal movement within the retraction tube. The retraction body has a rear portion mounted within the retraction tube and a front portion carrying a needle which extends from the mouth of the retraction tube. The biasing element tends to drive the retraction body back into the retraction tube by applying a retraction force to the retraction body. The extended exposed front portion of the retraction body comprises a connection surface adapted to releasably engage a catheter connector on the extended front portion of the retraction body. A hollow catheter connector is configured with a conforming connection surface which is frictionally and releasably mounted on the connection surface of the retraction body with sufficient holding force to resist the retraction force and restrain retraction. The connector is restrained by the retraction tube from movement in the retraction direction. When the catheter connector is separated from the retraction body by forcibly pulling and/or toggling the handle portion while holding the connector, the connector is separated from the front portion of the retraction body by loosening of the connection surface and the retraction body is immediately and automatically forced into the retraction tube by the biasing element, drawing the needle behind it.

The connection surface of the catheter connector and retraction body are preferably tapered to facilitate a force fit and preferably comprise an arcuate and continuous surface although it is contemplated that discontinuous and engaging surfaces on the exposed front portion of the retraction body and the connector can be used to frictionally engage and hold the retraction body until separation occurs. The exposed front portion of the retraction body preferably extends far enough into the hollow connector so that the device can be handled by the retraction tube without feeling any looseness between what may be regarded as the handle portion and the connector. Thus the connector fits directly onto the exposed front portion of the retraction body and holds it in place against the retraction force provided by a spring.

The second embodiment differs from the first embodiment in that the connector is releasably and frictionally engaged with an extended front portion of the handle comprising a retraction tube which in turn holds the retraction body with the needle extended. The retraction tube has a body portion with an opening in back and a front portion extending forwardly from the body portion comprising a plurality of arms surrounding a passageway between the arms leading into the body portion. A retraction body is mounted for lineal movement within the body portion of the retraction tube, the body being installable from the back, so that the front portion extends forwardly through the passageway between the arms and is exposed together with a needle extending forwardly from the front portion. Retraction force in a retraction direction is provided by a biasing spring mounted within the retraction tube.

A catheter connector slidingly installed over and frictionally held on the front portion of the retraction tube presses the arms thereby clamping the arms against the front portion of the retraction body and holds the retraction body in place against the compression of the spring. The arms and front portion of the retraction body each have a complimentary groove or protrusion which fit together when the arms are clamped or pressed by the catheter connector to hold the retraction body in its position for use. The arms are elongated forwardly and have an arcuate lip which serves as a protrusion while the front portion of the retraction body has an arcuate groove which fits the arcuate lip so that the complimentary arcuate protrusion and arcuate groove hold the retraction body and prevent it from retracting.

The arms are springing arms which normally spring open when they are not being pressed by the connector to relieve the protrusion from fitting in the groove. The retraction body self-retracts into the retraction tube upon hand separation of the catheter connector from the retraction tube. The retraction tube preferably has a continuous wall which includes the elongated arms. The arms preferably extend forwardly from a reduced diameter portion of the retraction tube which serves as a shelf on the interior to support the front end of a compression spring. A stepped portion of the retraction body larger than the passageway between the interior of the body and the arms serves as a stop for the retraction body during installation of the retraction body from the rear of the retraction tube. When the catheter is hand separated from the retraction tube, the retraction body automatically self-retracts into the retraction tube drawing the needle entirely into the tube behind it. Both embodiments preferably include a flash chamber on the retraction body which allows the user to detect when blood begins to flow by visual inspection of the flash chamber through the clear wall of the introducer.

Both embodiments are well suited for mass production by assembly of the retraction body from the rear of the retraction tube whereby a substantial portion of the retraction body is surrounded by the spring which is nearly as long as the interior of the retraction body and almost as great in diameter. Therefore, when the retraction body is pushed by means of a tool into the retraction tube, the retraction tube together with the portion of the retraction body contained within the center of the spring serves as a guide which prevents the spring from buckling or moving laterally. Once the retraction body is seated in the front of the retraction tube with the front exposed, the needle can be installed and then the connector frictionally engaged to hold the retraction body and the device is ready for use.

BRIEF DESCRIPTION OF THE DRAWINGS

FIG. 2 is a side elevation cut away through the center line of the assembled parts of FIG. 1;

FIG. 3 is a partial enlargement of FIG. 2 showing how the retraction body is held in the unretracted position by the catheter connector;

FIG. 4 is a partially cut away side elevation of the self-retracting catheter introducer of the previous Figures in the retracted position;

FIG. 5 is a front cross sectional view of a second embodiment of the invention on the lines 5—5 of FIG. 7;

FIG. 6 is a partial cut away side elevation of the second embodiment showing part of the catheter connector and retraction tube and all of the retraction body;

FIG. 8 is a partial cut away view of the working parts of FIGS. 5–7 showing partial retraction of the retraction body after the connector has been removed;

FIG. 9 is a partial cut away side elevation showing the second embodiment of FIGS. 5–8 in the fully retracted position after the retraction tube has been disconnected from the connector.

DETAILED DESCRIPTION OF THE PREFERRED EMBODIMENT

Figure 1:
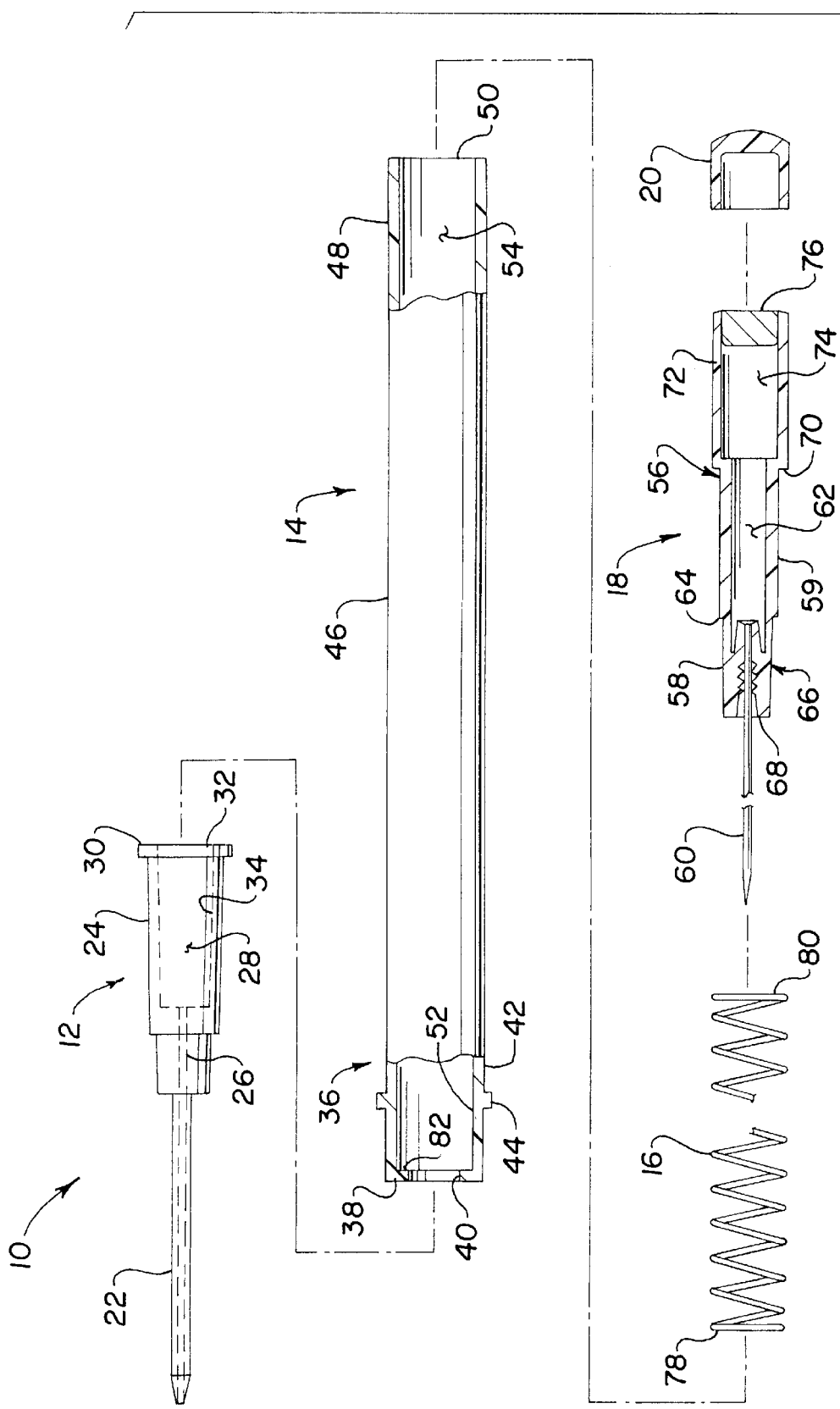
FIG. 1 is an exploded side elevation of a first embodiment of the invention showing the cannula and cannula connector, retraction tube, biasing element, retraction body and a closure element.

In the description that follows, like parts will be given the same reference numerals. The drawings of the preferred embodiments are generally true to scale and the parts are circular. Like parts in the second of the two embodiments may use the same reference numerals or the same number with a prime to indicate some variation.

FIG. 1 shows the exploded assembly of the self-retracting IV catheter introducer assembly 10 with the exception of the common protective cap that is placed over the needle. The cap (not shown) is only necessary because catheter introducers are shipped assembled ready for use. The main parts illustrated are the catheter connector assembly 12, retraction tube 14, biasing element 16, retraction body assembly 18 and closure element 20.

Catheter connector assembly 12 includes a flexible plastic or rubber cannula 22 and a connector 24 having a needle channel 26 and a hollow portion 28 having a flange 30 with an opening 32. Hollow opening 28 has a tapered inner surface 34 comprising a connection surface.

Retraction tube 14 has a front end portion 36 with a front end having a forwardly facing surface 38 and an opening 40 in the front end. Retraction tube 14 is preferably defined by a continuous wall 42 which may be provided with one or more stops 44 for a conventional protective cap over the needle. Tube 14 has an intermediate section 46 and a rear end portion 48 having an opening 50 in the rear end portion. Wall 42 has an inner surface 52 and defines an inner space or retraction space 54. As is conventional, the body is molded from clear plastic so the operator can see when the catheter is properly inserted in a patient. Biasing element 16 is preferably a coil spring.

Retraction body assembly 18 comprises a retraction body 56 having a front portion 58 carrying a catheter insertion needle 60 which is fixed in place. The internal center of front portion 58 has irregular openings in its center portion to assist in gluing the needle in place. The hollow needle creates a fluid passageway into a chamber 62 immediately behind front portion 58. A step 64 creates a slightly larger diameter in the central body portion of retraction body 56. A connection surface 66 is created along the outside surface of front portion 58 between the front 68 of front portion 58 and step 64. A second step 70 at the back of the intermediate portion of body 56 serves as a spring seat. It denotes the beginning of an enlarged rear portion 72 having an outer surface slightly smaller than the inside diameter of retraction tube 14 and encloses a flash chamber 74. Rear portion 72 has an open back end which is tightly fitted with a porous plug 76 for the passage of air displaced by fluid. Spring 16 has a front end 78 and a back end 80 which fits against spring seat 70. Spring 16 fits over reduced diameter intermediate body section 59.

FIG. 2 shows self-retracting catheter introducer assembly 10 in its assembled ready-to-use condition. After needle 60 is glued into the front of retraction body 18, spring 16 is mounted from the front over intermediate body section 59 of retraction body 18 with its back 80 against seat 70. This assembly is inserted from the rear through opening 50 of retraction tube 14 and spring 16 is compressed against a ledge 82 formed at the front of tube 14. The front portion 58 of retraction body 18 is then pushed through opening 40 and extended forwardly beyond the front of tube 14. The hollow catheter connector 24 is releasably mounted on the front part of the retraction body, preferably in a sliding friction fit between connection surface 66 and inner surface 34 which are mating surfaces. Catheter connector 24 holds retraction body 18 in place against the retraction force applied in the retraction direction by the compressed spring. Then a closure element or cap 20 is snugly fitted into opening 50 at the back of retraction tube 14 to make sure the retracting parts cannot come out of the retraction tube. Rear portion 72 of retraction body 56 is slightly smaller in diameter than the inside diameter of chamber 54 so the retraction body is free to slide in the lineal direction along the length of retraction body 14. Depending on the tightness of the fit, closure 20 may include a vent to permit the escape of trapped air.

FIG. 3 is an enlarged view which better shows the component parts illustrated in FIG. 2. It is shown in the assembled and ready-to-use position. Here front end 78 of spring 16 is compressed against ledge 82 and back end 80 of spring 16 is compressed against seat 70. Step 64 being slightly wider than opening 40 also fits against ledge 82. It can be seen that the inner surface or connection surface 34 of connector 24 fits tightly over outer surface or connection surface 66 of front portion 58 of retraction body 56. Connection surfaces 34, 66 fit tightly enough together to resist the retraction force applied against retraction body 56 by spring 16. Surfaces 34, 66 are preferably tapered forwardly to smaller diameter to facilitate a friction fit.

Cooperating abutments are provided between the connector and the retraction tube to resist this retraction force. These abutments are provided by means of a rearwardly facing surface 84 of flange 30 of connector 24 and forwardly facing surface 86 on the front end of retraction tube 14. These abutting surfaces come together and cooperate to prevent rearward movement in the retraction direction of connector 24 which thereby restrains retractable body 56. It is noted that front portion 58 of retraction body 56 extends well into hollow connector 24 with the surface 66 in contact with surface 34. As shown, front portion 58 extends about half way into hollow portion 28 of connector assembly 12. This provides for a desirable stable connection between the two parts which in combination with abutment surfaces 84, 86 avoids any feeling of looseness when the catheter introducer is handled. This is not a critical requirement, however, since the main requirement is that connector 24 be restrained by the retraction tube yet allow relatively easy hand separation of catheter connector assembly 12 from retraction body 56.

Since there is no actual sealing requirement between the connector and the retraction body, which has a completely internal fluid passageway, connection surface 66 does not necessarily need to be a continuous surface. It is contemplated that the one or both of the connection surfaces 34, 66 could be separated lands such as might be visualized running in the longitudinal direction or possibly a series of non-interlocking ridges or fins. It is contemplated that connection surface 66 and inner surface 34 may have complimentary engagement ridges (not shown) in the nature of course threads with a raised profile and a lowered profile on the complimentary part which requires a twist to separate the connector to initiate retraction. In such case it would be desirable to include a means for stopping rotation of the retractable retraction body internally of the retraction tube. A lateral extension in the vicinity of step 64 and a corresponding stop within tube 14 could be applied or the anti-rotation provided by a non-circular shape. All these variations are contemplated as a connection surface which releasably holds the retraction body by means of the connector with the spring compressed and where the retraction tube restrains the connector which in turn holds the retraction body. Disengagement of the connection surfaces immediately and automatically causes retraction.

FIG. 4 shows the completely retracted position. Cannula 22 at this point would be inserted into the patient with the connector ready for attachment to a tube for infusion of a fluid while retraction tube containing retraction body 56 and needle 60 would be discarded. Note that the retraction tube 14 is long enough to completely hold the retraction body and the entire insertion needle 60. The spring is preferably long enough in its uncompressed state to ensure that the retraction body is pushed back far enough into tube 14 that needle 60 is not exposed.

A second embodiment of the invention is shown in FIGS. 5–9. This embodiment is most easily understood by reference to FIG. 6. The second embodiment employs the same concept as the first embodiment in that there is immediate self-retraction when the retraction tube is hand separated from the connector, but in this embodiment the front of the retraction tube instead of the connector actually restrains the retraction body. The connector does not actually touch the retraction body in the second embodiment.

The main components of the second embodiment 10' are catheter connector assembly 12, retraction tube 14' and retraction body 18'. Retraction tube 14' has a body portion 88 having a wall 90 with a longitudinally extending tubular inner surface 92 and an opening 50' in back. Closure 20 stops opening 50' after retraction body 18' is installed into the retraction tube from the rear. In addition to body portion 88, tube 14' has a front portion 94 comprising a plurality of arms 96 surrounding a passageway 98 leading into body portion 88. Passageway 98 is occupied by the forwardly extending portion 58' of the retraction body to be described. Wall 90 is turned inwardly to form the ledge 82' where arms 96 begin. Arms 96 are elongated forwardly from ledge 82' and terminate in protrusions 100. Arms 96 have an arcuate outward surface 102 running from the front surface 86' of body portion 88 to protrusions 100. The arms have an arcuate inner surface 104 from which protrusions 100 extend inwardly toward the center line. The parts shown are symmetrical.

Retraction body assembly 18' comprises retraction body 56' having a flash chamber 74' with a porous plug 76. Retraction body 56' has a rear portion 72' nearly as large in diameter as space 54 within body portion 88 of tube 14'. Body 56' further includes a stepped down in diameter intermediate portion 59', beginning at step 70. Spring 16 has its front end 78 positioned behind ledge 82' and its back end 80 positioned in front of step 70 and surrounds intermediate body section 59'. There is a further stepped down in diameter portion 58' beginning at step 106 which comprises front portion 58' extending forwardly through passageway 98 between and within arms 96. Front portion 58' preferably extends beyond protrusions 100 to terminate at front end 68'. Front portion 58' has an arcuate outer surface 108 extending between step 106 and front end 68', which in the preferred embodiment is circular tapering to a smaller diameter from back to front. A groove 110 is depressed into surface 108 at a position along surface 108 to receive protrusions 100 which is the means by which retraction body 56' is held by arms 96 in the assembled for use position of FIG. 6. Irregular openings within front portion 58' receive adhesive to install and fix needle 60 extending forwardly through cannula 22 in fluid communication with flash chamber 74.

Referring now to FIGS. 5 and 7, a cut away portion of body portion 88 of retraction tube 14' shows in dotted outline retraction body 56' and compressed spring 16 wherein arms 96 are seen as having the arcuate outer surface 102 being clamped by the open back end portion of connector 24 thereby holding protrusions 100 into groove 110. The inner surface 34 of connector 24 is frictionally held in contact with outer surface 102. Outer surface 102 is preferably tapered to a smaller diameter outwardly like inner surface 34 of connector 24.

In FIG. 5, body 88 has a flange 112 wherein three arcuate arms 96 are shown separated by gaps 114. A portion of groove 110 is seen in dotted outline. Flange 112 includes a flat side 116 which conveniently prevents the assembled structure from rolling on a flat surface. Finally, a plurality of longitudinally extending fins 118 serve as support for a protective cap (not shown) which is installed on the front of the tube against flange 112. Front portion 58' extends forwardly through passageway 98 between the arms. The compressed biasing spring is applying a retraction force to the retraction body. Although flange 30 is shown pressing against front 86 of body portion 88, and this is a desirable configuration, it is seen that the resistance against retraction is applied solely by the engagement of protrusions 100 with groove 110. Thus it is the tube itself which holds the body. Although three arms 96 are illustrated, there could be more or less, so long as they are able to engage and hold the front of the retraction body.

FIG. 8 illustrates the partially retracted structure of FIG. 7 after connector 24 of connector assembly 12 has been removed. Here the arms 96 are seen to be springing arms which spring outwardly away from front portion 58' a sufficient distance to release protrusions 100 from groove 110. Arms 96 are molded to normally spring open when they are not being pressed by connector 24. Retraction tube 14' has a continuous wall 90 which forms the body portion 88 and the arms 96 wherein body 88 has a stepped portion 106 behind forwardly facing surface 86' which forms a reduced diameter portion of retraction tube 14' from which arms 96 extend. In FIG. 8, the entire retraction body 18' can be seen moving rearwardly within retraction tube 14' in the retraction direction under the influence of the now partially compressed spring 16.

FIG. 9 shows the completely retracted position of the structure of FIGS. 5–8. It is seen that retraction tube 14' is long enough to receive the entirety of the retracted body assembly 18' including the entirety of the needle 60 which is drawn in through the passageway 98 where it is no longer exposed.

In the best mode, the retraction tube and retraction body are preferably made from a clear molding grade of polypropylene that will enable the user to visually determine when there is flow into the flash chamber. The second embodiment requires material which has some flexibility and will take a "set" such that the arms will retain the ability to spring open to release the retraction body.

Both embodiments are particularly well suited for automated high speed molding manufacture and assembly. Beyond the porous plug, needle and closure cap, there are only two main parts and a conventional spring. The first embodiment has no undercuts that would require special molds and molding techniques and the second embodiment has only the groove 100 to contend with.

Assembly of the main components is from the rear. The spring can be inserted through the opening in the back of the retraction tube and the retraction body inserted preferably without the needle into the back of the spring which rests against stop 70. Then a plunger tool pushes against the back of the retraction body as it is moved forward in the tube compressing the spring. The combination of the retraction body being inside the spring in close support thereof and the spring being restrained by the retraction tube prevents buckling of the spring during high speed installation. The tube acts as a guide for the spring. After the retraction body is fully forward, it is held while needle 60 is glued in place. Then the needle is passed into the cannula and the catheter connector frictionally installed on the extended exposed front portion of the retraction body or in the case of the second embodiment, over the arms on the front of the retraction tube to hold the retraction body in place. Once this is done, the tool is removed from the retraction tube and end cap 20 is installed to retain the retracted parts after retraction. Although it is preferred that the needle be installed after the body is seated against the ledge in the tube, it is also possible to glue the needle in first, since the opening it must pass through is relatively large and slight curvature of the needle not likely to cause a "hang up" of the needle as it is moved forward.

The flange at the rear of the connector in the case of the second embodiment is preferably beveled to make it easy to push the connector over the outer ends of arms 96. It is expected that a conventional catheter connector and cannula can be used with both embodiments.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of he invention.

I claim:

1. A self-retracting IV catheter introducer, comprising:
   a retraction tube having an open front end;
   a retraction body slidingly mounted in the retraction tube, said body having a front portion carrying a fixed needle, the front portion and needle extending from the open front end of the retraction tube;
   a biasing element in the retraction tube applying a retraction force to the retraction body;
   a hollow catheter connector releasably mounted on the front portion of the retraction body, said retraction body being restrained from retraction by contact of the connector with the retraction tube;
   wherein the retraction body self-retracts into the retraction tube upon hand separation of the catheter connector from the retraction body.

2. The self-retracting IV catheter of claim 1 wherein the connector is releasably mounted by means of a sliding friction fit.

3. The self-retracting IV catheter of claim 2 wherein the connector has an opening that receives and holds the front portion of the retraction body and cooperating abutments are provided between the connector and the retraction tube to resist retraction force when the connector is drawn up against the retraction tube by the action of the biasing element.

4. The self-retracting IV catheter of claim 3 wherein said abutments are provided by means of a rearwardly facing surface on the connector and a forwardly facing surface on the front end of the retraction body.

5. The self-retracting IV catheter of claim 3 wherein the front portion of the retraction body has an outer surface which extends well into the hollow connector, which has an inner surface, wherein said inner and outer surfaces comprise a connection surface which releasably mount the connector on the retraction body.

6. The self-retracting IV catheter of claim 5 wherein the open front end of the retraction body has a ledge and said biasing element is a spring having a front end which rests against said ledge to apply retraction force to the retraction body.

7. The self-retracting IV catheter of claim 6 wherein said spring fits around a reduced diameter body portion of the retraction body and has a back end, the retraction body having a spring seat which receives the back end of the spring.

8. The self-retracting IV catheter of claim 7 wherein the retraction body includes a flash chamber located mainly inside the retraction tube, to detect when the catheter has been properly inserted.

9. A self-retracting IV catheter introducer, comprising:
 a retraction tube having a front end portion with an open mouth and a back end portion;
 a retraction body configured for lineal movement within the retraction tube, having a rear portion mounted within the retraction tube and a front portion carrying a needle and extending from the retraction tube;
 a biasing element tending to drive the retraction body into the retraction tube with a retraction force;
 a connection surface adapted to releaseably engage a catheter connector on the extended front portion of the retraction body; and
 a hollow catheter connector mounted on the connection surface with sufficient holding force to resist the retraction force, said connector being restrained from movement in the retraction direction by the retraction tube;
 wherein the retraction body is immediately self-retracted in response to retraction force applied by the biasing element upon separation of the connector from the retraction body thereby drawing the needle into the retraction tube.

10. The self-retracting IV catheter introducer of claim 9 wherein separation of the connector from the retraction body is accomplished by hand loosening of the connector and retraction body at the connection surface.

11. The self-retracting IV catheter introducer of claim 10 wherein the hollow end of the catheter connector and the connection surface of the retraction body are tapered to facilitate a force fit.

12. The self-retracting IV catheter introducer of claim 11 wherein the connection surface is a continuous surface.

13. The self-retracting IV catheter introducer of claim 10 wherein the hollow opening of the catheter connector has an inner surface and the connection surface of the retraction body engages a substantial portion of the inner surface.

14. The self-retracting IV catheter introducer of claim 9 wherein the front portion of the retraction body extending from the needleholder is grooved or split such that the connection surface is not continuous.

15. The self-retracting IV catheter introducer of claim 14 wherein the connection surface and the catheter connector have complementary engagement ridges which have a raised profile on one part and a lowered profile on the complementary part, with respect to the surface on which they reside, such that self-retraction will not occur without disengagement of the complementary engagement ridges.

16. A self-retracting IV catheter introducer, comprising:
 a retraction tube having a body portion with an opening in back and a front portion extending forwardly from the body portion, the front portion comprising a plurality of arms surrounding a passageway between the arms leading into the body portion;
 a retraction body having a front portion mounted for lineal movement within the body portion of the retraction tube, the retraction body being installable from the back of the retraction tube so that the retractor body front portion extends forwardly through the passageway between the arms, there being a needle extending forwardly from the front portion;
 a biasing spring mounted within the retraction tube having a compressed position to apply a retraction force to the retraction body;
 a catheter connector slidingly installed over and frictionally held on the front portion of the retraction tube to press the arms thereby clamping the arms against the front portion of the retraction body and holding the retraction body in place against the compression of the spring;
 whereby the retraction body self retracts into the retraction tube upon hand separation of the catheter connector from the retraction body.

17. The self-retracting IV catheter of claim 16 wherein the retraction tube and front portion thereof have a continuous wall.

18. The self-retracting IV catheter introducer of claim 16 wherein the arms are springing arms which normally spring open when they are not being pressed by said connector.

19. The self-retracting IV catheter introducer of claim 18 wherein the arms and the front portion of the retraction body each have a complementary groove or a protrusion which fit together when the arms are clamped by the catheter connector to hold the retraction body.

20. The self-retracting IV catheter of claim 19 wherein the arms are elongated forwardly and have an arcuate lip which serves as a protrusion and the front portion of said body has an arcuate groove which fits said lip so that when the catheter introducer is assembled and the connector slidingly installed over the arms, the arcuate protrusion and arcuate groove hold the retraction body and prevent it from retracting.

21. The self-retracting IV catheter of claim 20 wherein the retraction tube and front portion thereof have a continuous wall.

22. The self-retracting IV catheter introducer of claim 16 wherein the retraction tube has a continuous wall which forms the body portion and the arms wherein said arms extend forwardly from a reduced diameter portion of said retraction tube.

23. The self-retracting IV catheter introducer of claim 22 wherein said retraction body has a stepped portion behind the front portion which is larger than the reduced diameter section and serves as a stop for said body during installation of the retraction body from the rear of the retraction tube.

24. The self-retracting IV catheter introducer of claim 22 wherein the front portion of the retraction body extends beyond the arms of the retraction tube and both are covered by the catheter connector when the catheter connector is installed to press the arms of the retraction tube against the front portion of the retraction body.

25. The self-retracting IV catheter introducer of claim 22 wherein the spring has a front end which rests against a ledge created at the reduced diameter portion of the retraction body to apply retraction force to the retraction body.

26. The self-retracting IV catheter introducer of claim 25 wherein said spring fits around a reduced diameter body portion of the retraction body and has a back end, the retraction body having a spring seat which receives the back end of the spring whereby the spring is compressed between the seat and the ledge to apply said retraction force to the retraction body.

27. The self-retracting IV catheter of claim 26 wherein the retraction body has a back end portion which comprises a flash chamber located inside the retraction tube, to detect when the catheter has been properly inserted.

28. A self-retracting IV catheter introducer, comprising:

a retraction tube having a body portion and a front reduced diameter portion comprising springing parts and a passageway under the springing parts leading into the body portion;

a retraction body installable from the rear of the retraction tube, having a rear portion mounted within the body portion of the retraction tube and a front portion carrying a needle, the front portion slidable through the passageway under said springing parts;

a biasing element tending to drive the retraction body into the retraction tube with a retraction force;

cooperative engagement surfaces located on the front portion of the retraction body and the springing parts, which hold the retraction body when the surfaces are engaged;

a catheter connector having an open back end slidingly mounted over the springing parts thereby engaging the engagement surfaces to hold the retraction body relative to the retraction tube;

whereby the retraction body self-retracts upon hand separation of the catheter connector from the retraction tube.

\* \* \* \* \*